United States Patent

Schotland et al.

[11] Patent Number: 5,905,261
[45] Date of Patent: May 18, 1999

[54] IMAGING SYSTEM AND METHOD USING DIRECT RECONSTRUCTION OF SCATTERED RADIATION

[76] Inventors: John Carl Schotland, 316 Penn Rd., Wynnewood, Pa. 19096; Masaru Ishii, 2429 Locust St., Philadelphia, Pa. 19103

[21] Appl. No.: 08/937,715

[22] Filed: Sep. 25, 1997

Related U.S. Application Data

[63] Continuation-in-part of application No. 08/564,681, Dec. 1, 1995, abandoned.

[51] Int. Cl.$^6$ ..................................... G01N 21/64
[52] U.S. Cl. ...................... 250/341.8; 128/665
[58] Field of Search ............... 250/358.1, 330; 128/665, 663, 664

[56] References Cited

U.S. PATENT DOCUMENTS

| | | |
|---|---|---|
| 4,515,165 | 5/1985 | Carroll . |
| 4,948,974 | 8/1990 | Nelson et al. . |
| 5,070,455 | 12/1991 | Singer et al. . |
| 5,090,415 | 2/1992 | Yamashita et al. . |
| 5,148,022 | 9/1992 | Kawaguchi et al. . |
| 5,158,090 | 10/1992 | Waldman et al. . |
| 5,203,339 | 4/1993 | Knuttel et al. . |
| 5,213,105 | 5/1993 | Gratton et al. . |
| 5,275,168 | 1/1994 | Reintjes et al. . |
| 5,386,827 | 2/1995 | Chance et al. . |
| 5,528,365 | 6/1996 | Gonatas . |
| 5,747,810 | 5/1998 | Schotland ........................ 250/358.1 |

OTHER PUBLICATIONS

"Photon Hitting Density" by Schotland, Haselgrove, Leigh, (Feb. 1, 1993) Applied Optics vol. 32, No. 4.

"Diffusive Emission Tomography" by Schotland and Ishii, (Mar. 20, 1996) Trends in Optics and Photonics 2, 145 (1996).

*Primary Examiner*—Edward P. Westin
*Assistant Examiner*—Richard Hanig
*Attorney, Agent, or Firm*—John T. Peoples

[57] ABSTRACT

A method for the direct, mathematical reconstruction of the image of an object from measurements of the transmitted intensity of the scattered radiation effected by irradiating the object. The transmitted coefficient is related to the image by an integral operator. The image is directly, mathematical reconstructed by executing a prescribed mathematical algorithm, as determined with reference to the integral operator, on the transmitted coefficient, the algorithm further relating the absorption coefficient, the diffusion coefficient, or both to the transmitted coefficient by a different integral operator.

12 Claims, 6 Drawing Sheets

700

710 — ENABLE ENERGY SOURCE AND MEASURE TRANSMISSION COEFFICIENT AT DETECTOR

720 — COMPUTE SCATTERING DATA FROM TRANSMISSION COEFFICIENT

730 — COMPUTE FOURIER TRANSFORM OF SCATTERING DATA

740 — EFFECT SINGULAR VALUE DECOMPOSITION OF ABSORPTION OPERATOR

750 — EFFECT SINGULAR VALUE DECOMPOSITION OF DIFFUSION OPERATOR

760 — DIRECTLY COMPUTE ABSORPTION IMAGE USING REDUCED SCATTERING DATA

770 — DIRECTLY COMPUTE DIFFUSION IMAGE USING REDUCED SCATTERING DATA

780 — FOR MULTIPLE WAVEVECTORS, COMPUTE SUCCESSIVE PROJECTIONS CONVERGING TO ABSORPTION AND DIFFUSION IMAGES

FIG. 7

IMAGING SYSTEM AND METHOD USING DIRECT RECONSTRUCTION OF SCATTERED RADIATION

This application is a continuation-in-part application of U.S. patent application Ser. No. 08/564,681 filed Dec. 1, 1995, now abandoned.

FIELD OF THE INVENTION

This invention relates generally to a system, and concomitant methodology, for generating an image of an object and, more particularly, to such system and methodology for which the image is directly, mathematically reconstructed from measurements of predominantly diffusively scattered radiation detected by irradiating the object.

BACKGROUND OF THE INVENTION

The inventive subject matter addresses the physical principles and the associated mathematical formulations underlying the direct reconstruction method for optical imaging in the multiple scattering regime. The result is a methodology for the direct solution to the image reconstruction problem. Moreover, the method is generally applicable to imaging with any scalar wave in the diffusive multiple scattering regime and is not limited to optical imaging. However, for the sake of elucidating the significant ramifications of the present invention, it is most instructive to select one area of application of the method so as to insure a measure of definiteness and concreteness to the description. Accordingly, since many biological systems meet the physical requirements for the application of the principles of the present invention, especially photon diffusion imaging principles, the fundamental aspects of the present inventive subject matter will be conveyed using medical imaging as an illustrative application of the method.

There have been three major developments in medical imaging over the past 20 years that have aided in the diagnosis and treatment of numerous medical conditions, particularly as applied to the human anatomy; these developments are: (1) the Computer-Assisted Tomography (CAT) scan; (2) the Magnetic Resonance Imaging (MRI); and (3) the Positron Emission Tomography (PET) scan.

With a CAT scanner, X-rays are transmitted through, for example, a human brain, and a computer uses X-rays detected external to the human head to create and display a series of images—basically cross-sections of the human brain. What is being imaged is the X-ray absorption function for unscattered, hard X-rays within the brain. CAT scans can detect, for instance, strokes, tumors, and cancers. With an MRI device, a computer processes data from radio signals impinging on the brain to assemble life-like, three-dimensional images. As with a CAT scan, such malformations as tumors, blood clots, and atrophied regions can be detected. With a PET scanner, the positions of an injected radioactive substance are detected and imaged as the brain uses the substance. What is being imaged is the gamma ray source position. Each of these medical imaging techniques has proved invaluable to the detection and diagnosing of many abnormal medical conditions. However, in many respects, none of the techniques is completely satisfactory for the reasons indicated in the following discussion.

In establishing optimal design parameters for a medical imaging technique, the following four specifications are most important. The specifications are briefly presented in overview fashion before a more detailed discussion is provided; moreover, the shortcomings of each of the conventional techniques are also outlined. First, it would be preferable to use a non-ionizing source of radiation. Second, it would be advantageous to achieve spatial resolution on the order of a millimeter to facilitate diagnosis. Third, it would be desirable to obtain metabolic information. And, fourth, it would be beneficial to produce imaging information in essentially real-time (on the order of one millisecond) so that moving picture-like images could be viewed. None of the three conventional imaging techniques is capable of achieving all four specifications at once. For instance, a CAT scanner is capable of high resolution, but it uses ionizing radiation, it is not capable of metabolic imaging, and its spatial resolution is borderline acceptable. Also, while MRI does use non-ionizing radiation and has acceptable resolution, MRI does not provide metabolic information and is not particularly fast. Finally, a PET scanner does provide metabolic information, but PET uses ionizing radiation, is slow, and spatial resolution is also borderline acceptable. Moreover, the PET technique is invasive due to the injected substance.

The four specifications are now considered in more detail. With respect to ionizing radiation, a good deal of controversy as to its effects on the human body presently exists in the medical community. To ensure that the radiation levels are within what are now believed to be acceptable limits, PET scans cannot be performed at close time intervals (oftentimes, it is necessary to wait at least 6 months between scans), and the dosage must be regulated. Moreover, PET is still a research tool because a cyclotron is needed to make the positron-emitting isotopes. Regarding spatial resolution, it is somewhat self-evident that diagnosis will be difficult without the necessary granularity to differentiate different structures as well as undesired conditions such as blood clots or tumors. With regard to metabolic information, it would be desirable, for example, to make a spatial map of oxygen concentration in the human head, or a spatial map of glucose concentration in the brain. The ability to generate such maps can teach medical personnel about disease as well as normal functions. Unfortunately, CAT and MRI report density measurements—electrons in an X-ray scanner or protons in MRI—and there is not a great deal of contrast to ascertain metabolic information, that is, it is virtually impossible to distinguish one chemical (such as glucose) from another. PET scanners have the ability to obtain metabolic information, which suggests the reason for the recent popularity of this technique. Finally, imaging is accomplished only after a substantial processing time, so real-time imaging is virtually impossible with the conventional techniques.

Because of the aforementioned difficulties and limitations, there has been much current interest in the development of a technique for generating images of the distribution of absorption and scattering coefficients of living tissue that satisfy the foregoing four desiderata. Accordingly, a technique using low intensity photons would be safe. The technique should be fast in that optical events occur within the range of 100 nanoseconds—with this speed, numerous measurements could be completed and averaged to reduce measurement noise while still achieving the one millisecond speed for real-time imaging. In addition, source and detector equipment for the technique may be arranged to produce necessary measurement data for a reconstruction procedure utilizing appropriately-selected spatial parameters to thereby yield the desired one millimeter spatial resolution. Finally, metabolic imaging with the technique should be realizable if imaging as localized spectroscopy is envisioned in the sense that each point in the image is assigned an absorption spectrum. Such an assignment may be used, for example, to make a map of oxygenation by measuring the absorption spectra for hemoglobin at two different wavelengths, namely, a first wavelength at which hemoglobin is saturated, and a second wavelength at which hemoglobin is de-saturated. The difference of the measurements can yield a hemoglobin saturation map which can, in turn, give rise to tissue oxygenation information.

The first proposals for optical imaging suggested a mathematical approach (e.g., backprojection algorithm) that is similar to that used to generate X-ray computerized tomography images. Light from a pulsed laser is incident on the specimen at a source position and is detected at a detector strategically placed at a point to receive transmitted photons. It is assumed that the earliest arriving photons (the so-called "ballistic photons") travel in a straight line between the source and detector, and the transmitted intensity is used in a mathematical reconstruction algorithm. In effect, only unscattered incident waves are considered as being useful for forming an image of any objects embedded in the specimen and, accordingly, techniques are employed to eliminate scattered light from the detection process, such as arranging a detector with "fast gating time" to only process the earliest arriving photons. However, since it is known that the ballistic photons are attenuated exponentially, if the specimen has a thickness exceeding a predetermined value, imaging is virtually impossible in many practical situations.

The latest proposals for optical imaging are now directed toward imaging systems which use diffusively scattered radiation to reconstruct a representation of the interior of a specimen. Representative of prior art in this field is U.S. Pat. No. 5,070,455 issued to Singer et al (Singer) on Dec. 3, 1991. The system disclosed by Singer uses radiation, such as photons or other particles, which will be scattered to a significant degree by the internal structure of a specimen. In the system, a specimen is irradiated and measurements of the attenuated and scattered radiation are effected at a number of points along the exterior of the specimen. It has been determined by Singer that such measurements are sufficient to determine the scattering and attenuation properties of the various regions inside the specimen. In accordance with the disclosure of Singer, the interior of the specimen is modeled as an array of volume elements ("voxels"). Each voxel in the model of the specimen has scattering and attenuation properties which are represented by numerical parameters that can be mapped so as to generate several images of the interior of the specimen.

The particular technique used by Singer to reconstruct the interior of the specimen can best be characterized as an "iterative" procedure. This procedure is now described in some detail so as to pinpoint its shortcomings and deficiencies. After collecting the imaging data, the scattering and attenuation coefficients for the voxels are assigned initial values, which helps to shorten the computation process—but which is also the characteristic of iterative or non-direct solution to a mathematical minimization problem. Next, the system computes the intensity of light that would emerge from the specimen if the interior of the object were characterized by the currently assigned values for the scattering and attenuation coefficients. Then, the difference between the measured light intensities and the computed light intensities are used to compute an "error function" related to the magnitude of the errors of reconstruction. This error function (also called "cost function" in minimization procedures) is then minimized using a multi-dimensional gradient descent methodology (such as Fletcher-Powell minimization), i.e., the coefficients are modified so as to reduce the value of the error function.

The process of computing exiting light intensities based on the currently assigned values for the scattering and attenuation coefficients, and then comparing the differences between the computed values and measured values to generate a new approximation of the scattering and attenuation properties of the interior of the specimen, continues until the error function falls below a specified threshold. The final values of the scattering and attenuation coefficients from this process are then mapped so as to generate a series of images of the interior of the specimen, thereby depicting the attenuation and scattering characteristics of the specimen's interior—which presumably will disclose both normal and abnormal conditions.

Singer thus discloses a technique to reconstruct an image by inversion using an iterative minimization procedure. Such an approach is more formally characterized as a "heuristic", in contrast to an "algorithm", since no verification or proof of even the existence of a solution using the approach has been offered. There are essentially an infinite number of scattering and attenuation coefficients under such a regime, and there is absolutely no assurance that the particular coefficients determined using the iterative technique are the actual coefficients for the specimen's interior. Moreover, such a heuristic method has a high computational complexity which is exponential in relation to the number of voxels and which is, in turn, a characteristic of difficult optimization problems with many local minima. The computational complexity of such a approach renders the reconstruction method virtually useless for imaging.

The other approaches presented in the prior art are closely related to that presented by Singer. These approaches also effect an indirect inversion of the forward scattering problem by an iterative technique which provide little, if any, physical insight.

The art is devoid, however, of any analytical or mathematical techniques, such as inversion formulas, which obtain the reconstructed image of an object with a variable absorption coefficient, or with a variable diffusion coefficient, or with variations in both the absorption and diffusion coefficients.

SUMMARY OF THE INVENTION

These limitations and other shortcomings and deficiencies of conventional techniques are obviated, in accordance with the present invention, by devising a direct, mathematical reconstruction methodology, and concomitant system, to generate an image of an object under investigation. Whereas the standard approach to the image reconstruction problem effects an approximate inversion of the forward scattering problem by a numerical method, the approach in accordance with the present invention is an mathematical solution to the image reconstruction problem. Explicit inversion formulas are formed and obtain from the observation that it is possible to construct the singular value decomposition of the forward scattering operator within the diffusion approximation.

In accordance with the broad aspect of the present invention for imaging an object having a variable absorption coefficient, the object under study is irradiated and the transmission coefficient due predominantly to diffusively scattered radiation is measured at appropriate locations proximate to the object. The transmission intensity is related to the absorption coefficient by an integral operator. An image representative of the object is directly reconstructed by executing a prescribed mathematical algorithm, determined with reference to the integral operator, on the transmission coefficient. The algorithm further relates the absorption coefficient to the transmission coefficient by a different integral operator.

In accordance with the broad aspect of the present invention for imaging an object having a variable diffusion coefficient, the object under study is irradiated and the transmission coefficient due predominantly to diffusively scattered radiation is measured at appropriate locations proximate to the object. The transmission intensity is related to the diffusion coefficient by an integral operator. An image representative of the object is directly reconstructed by executing a prescribed mathematical algorithm, determined with reference to the integral operator, on the transmission coefficient. The algorithm further relates the diffusion coefficient to the transmission coefficient by a different integral operator.

In accordance with the broad aspect of the present invention for imaging an object having variable absorption and diffusion coefficients, the object under study is irradiated and the transmission coefficient due predominantly to diffusively scattered radiation is measured at appropriate locations proximate to the object. The transmission intensity is related to the absorption and diffusion coefficients by an integral operator. An image representative of the object is directly reconstructed by executing a prescribed mathematical algorithm, determined with reference to the integral operator, on the transmission coefficient. The algorithm further relates the absorption and diffusion coefficients to the transmission coefficient by a different integral operator.

The organization and operation of this invention will be understood from a consideration of the detailed description of the illustrative embodiment, which follows, when taken in conjunction with the accompanying drawing.

BRIEF DESCRIPTION OF THE DRAWING

FIG. 7 is a flow diagram for the direct, analytic reconstruction of the image of an object for variations in both absorption and diffusion.

The same element appearing in more than one FIG. has the same reference numeral.

DETAILED DESCRIPTION

To place in perspective the detailed description of the present invention and thereby highlight the departure from the art as disclosed and claimed herein, it is both instructive and informative to first gain a basic understanding of the imaging environment in which the present invention operates by presenting certain foundational principles pertaining to the subject matter in accordance with the present invention. Accordingly, the first part of the description focuses on a high-level discussion of the imaging systems relevant to the inventive subject matter; this approach has the advantage of introducing notation and terminology which will aid in elucidating the various detailed aspects of the present invention. After this overview, the system aspects of the present invention, as well as the concomitant methodology, are presented with specificity.

OVERVIEW OF THE PRESENT INVENTION

Multiple scattering of light presents a fundamental physical obstruction to optical imaging. The inventive subject matter of the present invention addresses this phenomena, with the surprising result that diffusive light contains sufficient information to image the optical diffusion and absorption coefficients of a highly scattering medium. This conclusion is based on an integral equation formulation of inverse scattering theory that is applicable to multiple scattering in the diffusion limit. Using this representation, the first direct, mathematical reconstruction procedure ever devised for imaging the optical diffusion and absorption coefficients of a diffusively scattering medium is elucidated. In contrast to techniques which utilize unscattered (ballistic) photons for image formation, the procedure in accordance with the present invention allows for the imaging of objects whose size is large compared to the average scattering mean free path.

The familiar opaque or cloudy appearance of many objects having impinging light may be explained by the phenomenon of multiple light scattering. (It is to be noted that terminology will be generalized hereinafter so that an "object" is the physical manifestation of what is under study—such an object may stand alone, may be embedded in a specimen or a sample; in any case, the context of the descriptive material about an object will be set forth with clarity the meaning to be attached to the generic term "object" in that context.) The disclosure and teachings of the present invention address the problem of imaging an extended object that is embedded in a highly scattering medium.

Figure 1:
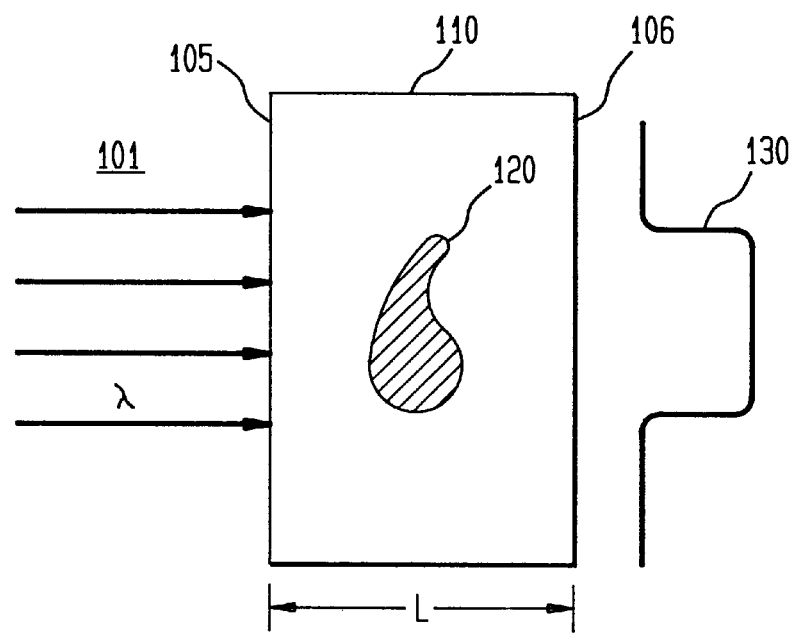
FIG. 1 depicts the transmission of light through a specimen containing an absorbing object in the ballistic limit.

For illustrative purposes, the case of only an absorbing object is considered. To elucidate the direct, analytic reconstruction process at its most fundamental level, a simplified system to which direct, analytic reconstruction is applicable is first described, namely, one in which a plane wave of light (photons) of wavelength $\lambda$ is incident upon a sample of linear dimension L that contains a spatially-extended object characterized by a position-dependent optical absorption coefficient; the width L is aligned with the impinging incident wave. If it is further assumed that photons are scattered by particles whose size is large compared to $\lambda$, then the scattering is described by a transport mean free path, designated $l^*$; the mean free path characterizes the average distance a photon travels before its direction is randomized. In the single-scattering regime, that is, where $l^* \gg L$, it is observed that most of the incident wave is unscattered upon exiting the sample and thus may be used to form a projection image of the diffusing object; this effect is depicted in FIG. 1. In FIG. 1, light rays 101 of wavelength $\lambda$ impinge on front 105 of sample 110 containing diffusing object 120, wherein the light rays transmitted through sample 100 exiting back 106 of sample 110 form a projection image represented by trace 130. The transmitted intensity represented by trace 130 is related to the line integral of the optical absorption coefficient along the direction of propagation of the unscattered wave. This gives rise to the so-called Radon transform of the absorption coefficient. By inversion of the Radon transform, it is possible to recover the absorption coefficient and thus an image of diffuser 120 is reconstructed. As already alluded to above, all commercially available imaging techniques are based on this simple physical principle.

Figure 2:
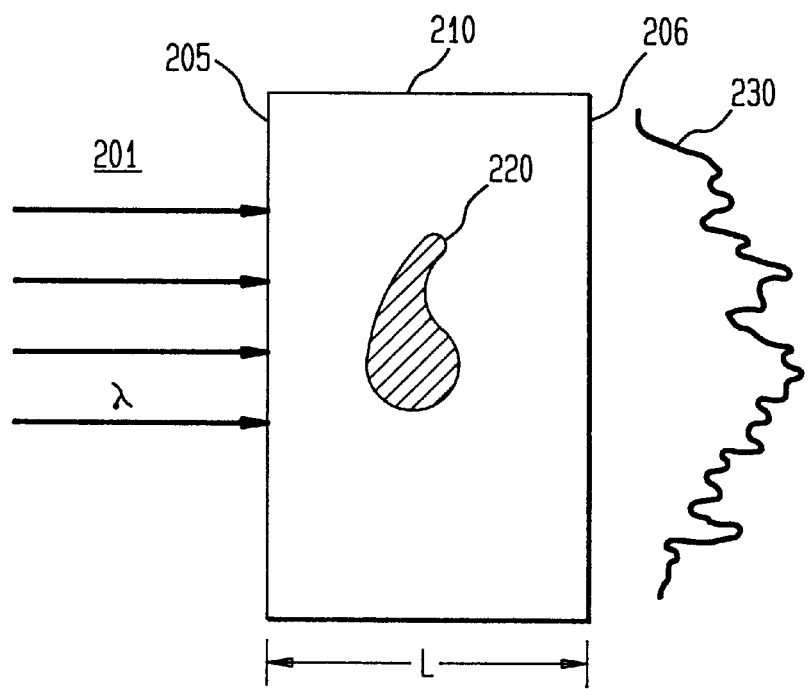
FIG. 2 depicts the transmission of light through a specimen containing an absorbing object in the diffusion limit.

In the multiple-scattering regime, that is, where $l^* \ll L$, a wave scatters many times while traversing the sample. In this situation, with $\lambda \ll l^*$, the path of a single photon may be described as a diffusive random walk where $D = \frac{1}{3}(c/n)l^*$ is a suitable diffusion constant, with c being the speed of light, n being the index of refraction, and c/n being the speed of light in the medium of the sample. The unscattered, or ballistic photons, are exponentially attenuated with a static transmission coefficient $T_{ball} \sim \exp(-L/l^*)$. The dominant contribution to the transmitted intensity is provided by diffusive photons with a diffusive transmission coefficient $T_{diff} \sim l^*/L$ which, even with coherent illumination, forms a complicated interference pattern that does not contain a simple image of the sample; such a pattern is illustrated in FIG. 2 (which has essentially the same pictorial representation as FIG. 1, except that the physical system of FIG. 2 is such that $l^* \ll L$ as contrasted to $l^* \gg L$ in FIG. 1). In FIG. 2, light rays 201 of wavelength $\lambda$ impinge on front 205 of sample 210 and eventually exit sample 210 from back 206. Absorbing object 220 gives rise to trace 230, which is representative of the complicated transmitted light pattern exiting back 206. In accordance with the present invention, there is devised a closed-form procedure for utilizing the information in such complicated patterns as exhibited by trace 230 to locate an object and thus perform optical imaging in the multiple-scattering regime.

Indeed, it has frequently been pointed out in the prior art that ballistic photons convey the least distorted image information while diffusive photons lose most of the image information. For this reason several elegant experimental techniques have been designed to select the ballistic photon contribution either by optical gating, holography, or filtering of the diffusive photons by optical diffusion. There is, however, an intrinsic physical limitation of any technique that relies solely on ballistic photons. This may be appreciated by considering the exponential attenuation of ballistic photons relative to the mild algebraic attenuation of diffusive photons. In particular, if the sample size L is sufficiently large compared to $l^*$, then $T_{ball}$ will fall below an experimentally measurable threshold (e.g., if $l^*$ is about 0.5 millimeters, then the attenuation is proportional to $e^{-40}$ in only 2 centimeters).

Thus, the likelihood of now reconstructing important and valuable images heretofore believed to be virtually impossible to reconstruct provides a strong motivation to overcome the limitations of ballistic imaging by employing multiply scattered diffusive photons for image reconstruction. From fundamental physical principles, such a direct, analytic reconstruction from the interference pattern of diffusive transmitted light is attainable since such a reconstruction is uniquely determined by two parameters, namely, the absorption and diffusion coefficients of the highly scattering system.

A. FUNCTION THEORETIC BASIS

By way of reiteration, we consider the problem of imaging the optical properties of a highly scattering medium probed by diffusing waves. An analytic solution to this inverse scattering problem is presented in the form of explicit inversion formulas.

Multiple scattering of light presents a fundamental physical obstruction to optical imaging. The existence of such multiple scattering leads to the breakdown of geometrical optics and has motivated the considerable recent interest in developing tomographic methods for imaging in highly-scattering systems. As alluded to in the foregoing discussion, two conceptually different approaches to this problem are currently under investigation. In the first approach, referred to as ballistic imaging, unscattered photons are selected by an optical gate and are then used for image formation. The intensity of such unscattered radiation is highly attenuated, and thus this approach is subject to practical limitations beyond which there is no way to improve its performance. The second, more powerful approach is to directly use the scattered radiation for image reconstruction. Here, in the usual formulation of the image reconstruction problem, the diffusive nature of multiply-scattered light is exploited to effect an approximate inversion of the forward scattering problem by a numerical method. This approach, however, is severely limited by the computational complexity of the inversion procedure.

Figure 3:
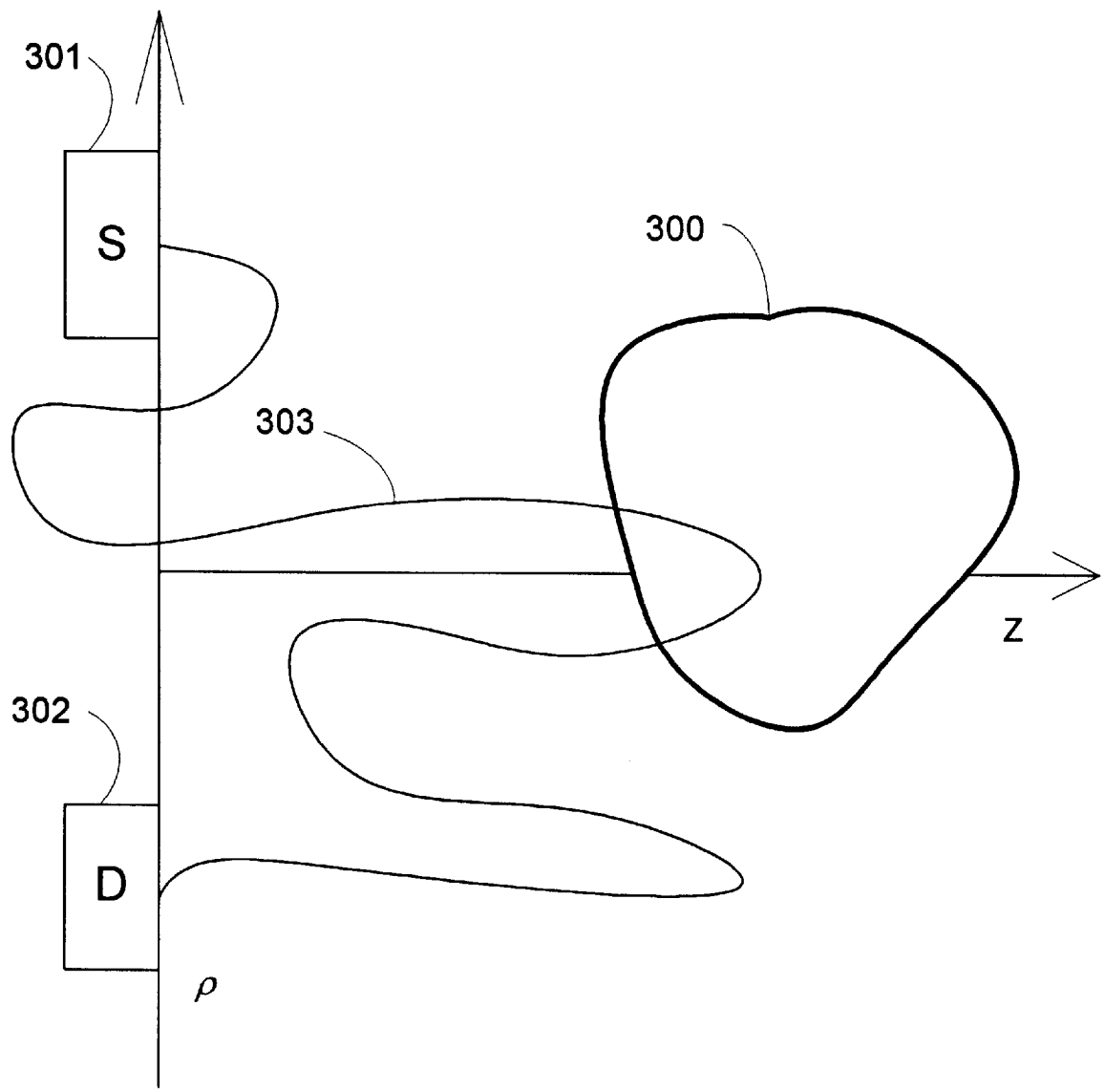
FIG. 3 illustrates the physical arrangement of an object wherein a diffusing wave is incident upon a highly-scattering object.

In this detailed description, we describe an analytic inverse scattering method that may be used to reconstruct the optical absorption and diffusion coefficients of a highly-scattering system probed by diffusive light. As shown in FIG. 3, diffusing wave 303 is incident upon highly-scattering object 300 in the half space $z > 0$ of an infinite medium wherein source 301 and detector 302 are located on the plane $z = 0$ with transverse coordinate $\rho$. The near-field intensity of the scattered diffusing wave is then measured on a surface adjacent to the object and is used as the data in the inverse scattering procedure. The results have the form of explicit inversion formulas which may be systematically improved by an iterative procedure. This method has distinct computational advantages in addition to providing insight into the structure of the inverse problem.

This detailed description is organized as follows. In Part I we derive the integral equations that describe the forward scattering problem within the diffusion approximation. In Part II we consider the image reconstruction problem in the backscattering geometry as a means of introducing the methods that are further developed in Part III to treat the general inverse problem.

I.) INTEGRAL EQUATIONS

Consider an experiment in which light from an amplitude-modulated source propagates in a highly-scattering medium characterized by an optical absorption coefficient $\alpha(r)$ and a photon diffusion coefficient $D(r)$. In this situation, the transport of light can be regarded as occurring by means of a diffusing wave whose energy density $u(r,t)$ satisfies the equation $$\partial_t u(r,t) = \nabla \cdot (D(r)\nabla u(r,t)) - \alpha(r)u(r,t) + S(r,t) \tag{1}$$

where $S(r,t)$ is the power density of the source. If the source has amplitude $A \leq 1$ and modulation frequency $\omega$ then $$S(r,t) = (1 + Ae^{-i\omega t})S(r) \tag{2}$$

where $S(r)$ is the unmodulated source power density. If $u(r,t)$ is decomposed into a zero-frequency component $u_0(r)$ and a frequency-dependent component $u_\omega(r)$ by $$u(r,t) = u_0(r) + Ae^{-i\omega t}u_{10\bar{7}}(r) \tag{3}$$

then $u_{10\bar{7}}(r)$ obeys the equation $$\nabla \cdot (D(r)\nabla u_\omega(r)) + (i\omega - \alpha(r))u_{10\bar{7}}(r) + S(r) = 0 \tag{4}$$

Figure 4A:
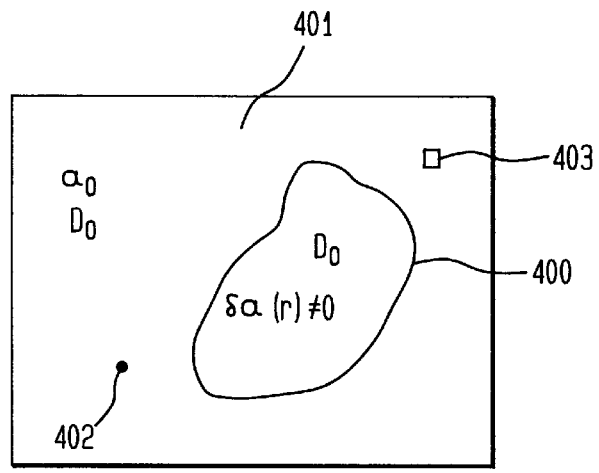
FIGS. 4A–4C depicts an object embedded in a medium for the cases of constant diffusion, constant absorption, and variable absorption and diffusion, respectively.
Figure 4B:
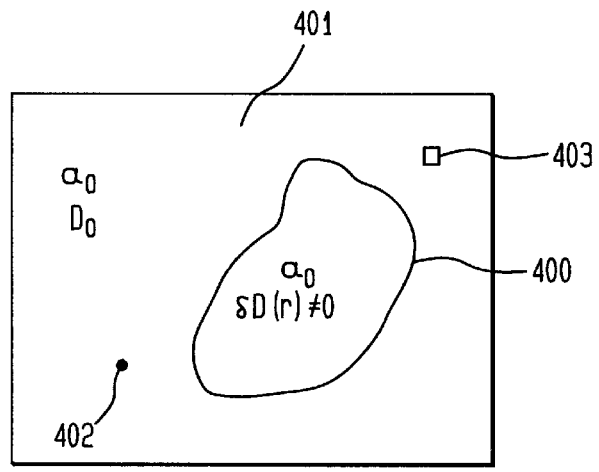
Figure 4C:
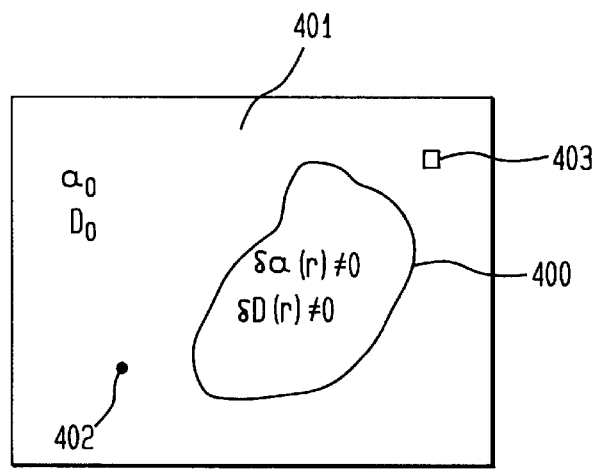

Note that $u_0(r)$ also obeys equation (4) with $\omega = 0$. The solution to equation (4) may be expressed in terms of the diffusion Green's function $G(r,r')$. Using standard perturbative methods the Green's function may be obtained from the Dyson equation $$G(r_1,r_2)=G_0(r_1,r_2)-\int d^3r(G_0(r_1,r)G(r,r_2)\delta\alpha(r)+\nabla_r G_0(r_1,r)\cdot\nabla_r G(r,r_2)\delta D(r)) \quad (5)$$

where $G_0(r_1,r_2)$ is the unperturbed Green's function for a homogeneous reference medium with absorption $\alpha_0$ and diffusion coefficient $D_0$. Here $\delta\alpha(r)=\alpha(r)-\alpha_0$ and $\delta D(r)=D(r)-D_0$ denote the spatial fluctuations in the absorption and diffusion coefficients away from their values in the reference medium. The diagram of FIG. 4A depicts these relations, namely, object 400 is shown immersed in medium 401 which has constant absorption coefficient $\alpha_0$ and constant diffusion coefficient $D_0$; object 400, on the other hand, has a fluctuating absorption coefficient $\alpha(r)\neq\alpha_0$ but constant diffusion coefficient $D_0$. In FIG. 4B, object 400 has constant absorption coefficient $\alpha_0$, but fluctuating diffusion $D(r)=0$. In FIG. 4C, on the other hand, object 400 has absorption $\alpha(r)\neq 0$ and diffusion $D(r)\neq 0$. (Also shown for completeness is $i^{th}$ source 402 and $j^{th}$ detector 403 surrounding object 400 in FIG. 4A).

The transmission coefficient $T(r_1,r_2)$ of a diffusing wave generated by a point source at $r_1$ and detected at $r_2$ is defined as the transmitted intensity of the frequency-dependent component of the wave normalized by the intensity that would be measured in the reference medium. Equation (5) may be used to obtain an integral equation for the transmission of the form $$T(r_1,r_2)=1-\int d^3r(\Gamma_A(r;r_1,r_2)\delta\alpha(r)+\Gamma_D(r;r_1,r_2)\delta_D(r)) \quad (6)$$

where $$\Gamma_A(r;r_1,r_2) = \frac{1}{G_0(r_1,r_2)}G_0(r_1,r)G(r,r_2) \quad (7)$$

and $$\Gamma_D(r;r_1,r_2) = \frac{1}{G_0(r_1,r_2)}\nabla_r G_0(r_1,r)\cdot\nabla_r G(r,r_2), \quad (8)$$

where $\Gamma_A(r;r_1,r_2)$ and $\Gamma_D(r;r_1,r_2)$ are the absorption and diffusion kernels, respectively. Equation (6) is an exact expression for the transmission that may be used to generate a perturbative expansion in $\delta\alpha(r)$ and $\delta D(r)$. Standard diagrammatic techniques may be used to resum this expansion with the result that to first order $$-\ln T(r_1,r_2)=\int d^3r(\Gamma_A^{(1)}(r;r_1,r_2)\delta\alpha(r)+\Gamma_D^{(1)}(r;r_1,r_2)\delta D(r)) \quad (9)$$

where $$\Gamma_A^{(1)}(r;r_1,r_2) = -\frac{\delta\ln T(r_1,r_2)}{\delta\alpha(r)} \quad (10)$$

or $$\Gamma_A^{(1)}(r;r_1,r_2) = \frac{1}{G_0(r_1,r_2)}G_0(r_1,r)G_0(r,r_2)$$

and $$\Gamma_D^{(1)}(r;r_1,r_2) = -\frac{\delta\ln T(r_1,r_2)}{\delta D(r)} \quad (11)$$

or $$\Gamma_D^{(1)}(r;r_1,r_2) = \frac{1}{G_0(r_1,r_2)}\nabla_r G_0(r_1,r)\cdot\nabla_r G_0(r,r_2)$$

with the functional derivatives evaluated at $\delta\alpha(r)=\delta D(r)=0$.

Figure 5A:
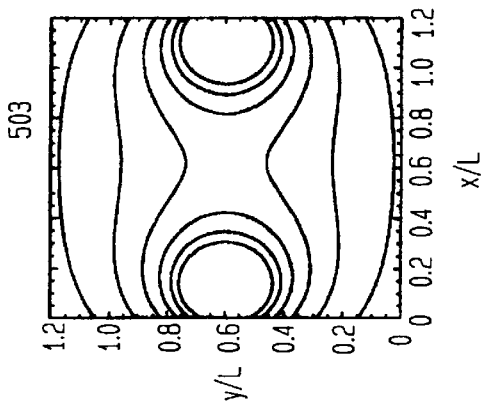
FIGS. 5A–5F depicts plots of the absorption kernel and diffusion kernel for several values of modulation frequency.
Figure 5B:
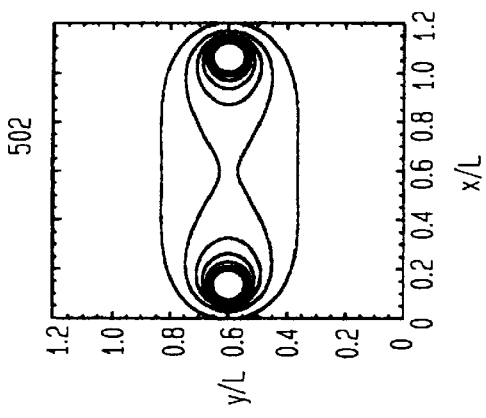
Figure 5C:
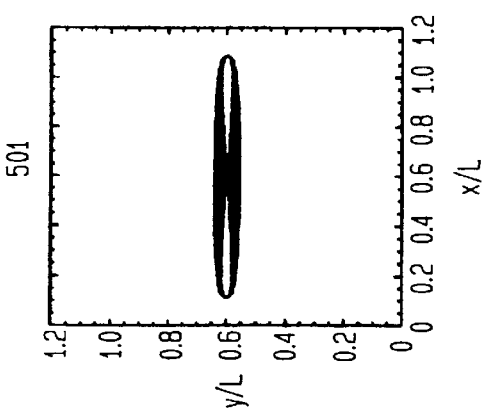
Figure 5D:
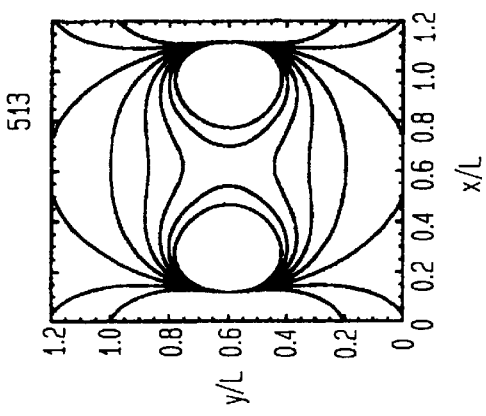
Figure 5E:
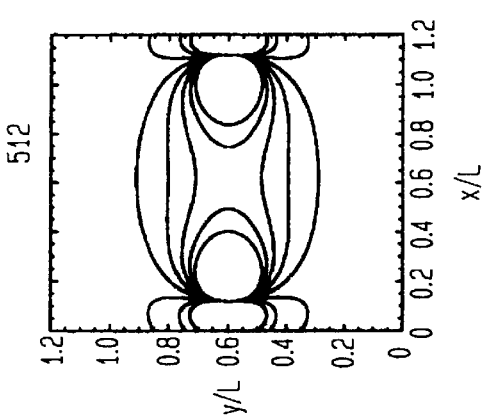
Figure 5F:
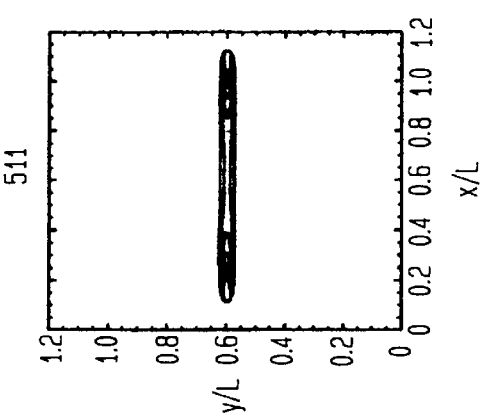

It is readily appreciated that equation (9) may be interpreted as a generalization of the Radon transform of conventional tomography. Recall that the Radon transform relates the transmission coefficient to the absorption by the line integral $$-\ln T = \int_L \mu(r)dr \quad (12)$$

where $\mu(r)=\alpha(r)/c$ and L is the line along which the incident wave propagates. By comparison, in equation (9), when the diffusion coefficient is homogeneous, the transmission is related to the integral of the absorption weighted by the kernel $\Gamma_A^{(1)}(r;r_1,r_2)$. This observation is further clarified by examining FIGS. 5A–5C in which contour plots of $\Gamma_A^{(1)}(r;r_1,r_2)$ in an infinite nonabsorbing medium are shown for several values of the modulation frequency $\omega$—in particular, $\omega\tau_D$ equal to 10,000, 100, and 1, respectively. (Here $\tau_D=L^2/D$ where L denotes the source-detector pair separation.) Contour plots of $\Gamma_D^{(1)}(r;r_1,r_2)$ are also shown for comparison in FIGS. 5D–5F. Note that in the geometrical limits, when the wavenumber $k=((\alpha_0-i\omega)/D)^{1/2}$ is sufficiently large, that $\Gamma_A^{(1)}(r;r_1,r_2)$ is concentrated along the line joining the source and detector and we therefore recover the results of classical tomography.

To simplify the analysis, for the remainder of this discussion, assume that the sample to be imaged is immersed in an effectively infinite homogeneous medium with absorption $\alpha_0$ and diffusion coefficient $D_0$. Further assume that the source and detector positions are fixed on the plane z=0 as shown in FIG. 3. Other geometries are also readily treated. To this end denote by $\rho_1$ and $\rho_2$ the transverse coordinates of the source and detector, and by $\phi(\rho_1,\rho_2)$ and $K(\rho,r')$ the restrictions of $-G_0(r_1,r_2)\ln T(r_1,r_2)$ and $G_0(r,r')$ to the measurement surface. In this notation, equation (9) may be rewritten as an integral equation for the scattering data $\phi(\rho_1,\rho_2)$ which is given by $$\phi(\rho_1,\rho_2)=\int d^3r(K(\rho_1,r)K(\rho_2,r)\delta\alpha(r)+\nabla_r K(\rho_1,r)\cdot\nabla_r K(\rho_2,r)\delta D(r)). \quad (13)$$

To facilitate our discussion we introduce the Fourier transform of the scattering data $\phi_q(\rho_1)$ which is defined by $$\phi_q(\rho_1)=\int d^2\rho_2 e^{iq\cdot\rho_2}\phi(\rho_1,\rho_2) \quad (14)$$

Thus equation (13) becomes $$\phi_q(\rho_1)=\int d^3r(K_q^A(\rho_1,r)\delta\alpha(r)+K_q^D(\rho_1,r)\delta D(r)) \quad (15)$$

where $$K_q^A(\rho_1,r) = \frac{1}{2D_0}e^{iq\cdot\rho_1}(q^2+k^2)^{-\frac{1}{2}}\exp\left[-(q^2+k^2)^{\frac{1}{2}}|z|\right]K(\rho_1,r) \quad (16)$$

and $$K_q^D(\rho_1,r) = \frac{1}{2D_0}e^{iq\cdot\rho_1}(q^2+k^2)^{-\frac{1}{2}} \quad (17)$$

$$\exp\left[-(q^2+k^2)^{\frac{1}{2}}|z|\right]\left(i\vec{q}-(q^2+k^2)^{\frac{1}{2}}\hat{z}\right)\cdot\nabla_r K(\rho_1,r),$$

where $\vec{q}=(q,0)$, that is, $\vec{q}$ is three dimensional. In deriving equations (16) and (17)), we have used the Fourier integral representation of $G_0(r_1,r_2)$ which is given by $$G_0(r_1,r_2) = \int d^3k \frac{e^{ik\cdot(r_1-r_2)}}{D_0 k^2+\alpha_0-i\omega} \quad (18)$$

or $$G_0(r_1,r_2) = \frac{1}{4\pi D_0}\frac{e^{-k|r_1-r_2|}}{|r_1-r_2|}$$

It is important to note that the descriptions of the scattering experiment in terms of $\phi_q(\rho_1)$ or $\phi(\rho_1,\rho_2)$ are equivalent.

II.) BACKSCATTERING

In the diffusive inverse scattering problem we wish to reconstruct the absorption and diffusion coefficients from the intensity of the diffusing wave measured on a surface adjacent to the sample. The approach to this problem described here involves the construction of explicit inversion formulas for the integral equation (9). In this section we consider the most elementary case in which an inversion of equation (9) is possible. This occurs in the backscattering geometry where source and detector positions coincide. Note that for backscattering the diffusion approximation breaks down and so we are mainly concerned here with illustrating those generic features of the inverse problem which carry over to the general case. To proceed, we observe for backscattering that the integral equation (9) becomes $$\bar{\alpha}(r) = \int d^3r' G_k^2(r,r') \delta\alpha(r') \tag{19}$$

where $\bar{\alpha}(r) = -\lim_{r \to r'} G_0(r,r') \ln T(r,r')$, the dependence on the wavenumber k has been made explicit, and we have assumed that the diffusion coefficient is spatially uniform. Next, we observe that if the identity $$\frac{\partial}{\partial k} G_k^2(r, r') = -\frac{1}{2\pi} D G_{2k}(r, r') \tag{20}$$

is applied to equation (19) we obtain the integral equation $$\phi(r) = \int d^3r G_{2k}(r,r') \delta\alpha(r') \tag{21}$$

where $\phi(r) = -2\pi D \partial \bar{\alpha}(r) / \partial k$.

Consider the integral equation (21) when k=0. This corresponds to the unmodulated continuous wave (cw) case without background absorption. Here the kernel in equation (21) assumes the form of the electrostatic potential for a point charge and thus $$\phi(r) = \frac{1}{4\pi D} \int d^3 r' \frac{\alpha(r')}{|r - r'|}. \tag{22}$$

Pursuing this electrostatic analogy further we see that the absorption plays the role of the charge density and $\phi(r)$ that of the potential. Thus the cw problem can be mapped onto an inverse problem in potential theory. This inverse problem is composed of recovering the charge density when the potential is specified on a surface. Clearly this problem is ill-posed because of the existence of charge densities whose contribution to the potential can be made to vanish on an arbitrary surface. Nevertheless, a suitably defined unique solution to the inverse problem will be constructed.

Returning now to the general backscattering problem we consider the geometry introduced earlier with source and detector positions fixed on the plane z=0. Then equation (21) becomes $$\phi_P(\rho) = \int d^3r' K_{2k}(\rho, r') \delta\alpha(r') \tag{23}$$

where $\phi_P(\rho) = \phi(\rho, 0)$. The image reconstruction problem has now been reduced to solving the integral equation (23) when $\phi_P(\rho)$ is specified. The solution to this equation may be obtained from the singular value decomposition of the operator $K_k(\rho, r')$. To this end we introduce the identity $$K_k(\rho, r') = \frac{1}{2D_0} \int \frac{d^2q}{(2\pi)^2} e^{iq \cdot (\rho - \rho')} (q^2 + k^2)^{-\frac{1}{2}} \exp\left[-(q^2+k^2)^{\frac{1}{2}}|z'|\right] \tag{24}$$

which follows from the Fourier integral representation equation (18) of $G_0(r,r')$ Equation (24) may now be rewritten as $$K_k(\rho, r') = \int d^2 q \sigma_q g_q(\rho) f_q^*(r') \tag{25}$$

where $$g_q(\rho) = \frac{1}{2\pi} e^{iq \cdot \rho} \tag{26}$$

$$f_q(r) = \frac{N_q}{2\pi} e^{i(q \cdot \rho + \theta_q)} \exp\left[-\left((q^2 + k^2)^{\frac{1}{2}}\right)^* |z|\right] \tag{27}$$

and $$\sigma_q = \frac{1}{2DN_q} \left[\left(q^2 + \frac{\alpha_0}{D}\right)^2 + \frac{\omega^2}{D^2}\right]^{-\frac{1}{4}} \tag{28}$$

with $$\tan(2\theta_q) = \frac{\omega}{Dq^2 + \alpha_0} \tag{29}$$

$$N_q^2 = \frac{1}{\sqrt{2}} \left[\left(\left(q^2 + \frac{\alpha_0}{D}\right)^2 + \frac{\omega^2}{D^2}\right)^{\frac{1}{2}} + q^2 + \frac{\alpha_0}{D}\right]^{\frac{1}{2}}. \tag{30}$$

It is readily verified that equation (25) defines the singular value decomposition of $K_{2k}(\rho, r')$ with singular values $\sigma_q$ since $K_{2k}^* K_{2k} f_q = \sigma_q^2 f_q$ and $K_{2k} f_q = \sigma_q g_q$. This result may be used to obtain the solution to the integral equation (23) in the form $$\delta\alpha(r) = \int d^2\rho' K_{2k}^+(r, \rho') \phi_P(\rho') \tag{31}$$

where the generalized inverse $K_{2k}^+(r, \rho')$ of $K_{2k}(\rho, r')$ is given by $$K_{2k}^+(r, \rho') = \int d^2 q \frac{1}{\sigma_q} g_q^*(\rho') f_q(r). \tag{32}$$

Combining equations (30) and (31), we obtain $$\delta\alpha(r) = \frac{D}{2\pi} \int d^2 \rho' \int_0^\infty dq q N_q^2 (q^2 + 4k^2)^{\frac{1}{2}} \tag{33}$$
$$J_0(q|\rho - \rho'|) \exp\left[-(q^2 + 4k^2)^{\frac{1}{2}}|z|\right] \phi_P(\rho')$$

which is the inversion formula for the diffusive inverse scattering problem in the backscattering geometry.

III.) INVERSE PROBLEM

In this section we consider the general inverse scattering problem for diffusing waves. The approach we will take is similar to that developed for backscattering in that the inverse problem will be solved by constructing the singular value decomposition of the forward scattering operator. The image reconstruction problem now consists of solving the integral equation equation (13) for $\delta\alpha(r)$ and $\delta D(r)$ when $\phi(\rho_1, \rho_2)$ is specified. Alternatively, since the Fourier transformed scattering data $\phi_q(\rho_1)$ contains the same information as the scattering data itself, we can reconstruct $\delta\alpha(r)$ and $\delta D(r)$ from the integral equation (15). We describe two approaches to this problem. In the first approach, for a single fixed value of the wavevector q we construct the singular value decomposition of the operator $K_q(\rho_1, r)$ and thereby solve the integral equation (15). The difficulty here is that we are reconstructing the functions $\delta\alpha(r)$ and $\delta D(r)$ of a three-dimensional argument from $\phi_q(\rho_1)$ which is a function of a two-dimensional argument. As a consequence, it is expected that this form of the inverse problem is ill-posed. In the second approach, we systematically improve upon the first approach by making use of the scattering data for a finite number of wavevectors, and thereby overcome the problem of recovering three-dimensional information from two-dimensional data.

A. Single Wavevector Solutions

We first consider the problem of reconstructing the absorption in a medium with a spatially uniform diffusion coefficient. In this situation the Fourier transformed scattering data satisfies the integral equation $$\phi_q(\rho_1) = \int d^3 r K_q^A(\rho_1, r) \delta\alpha(r). \quad (34)$$

As before, the solution to equation (34) may be obtained from the singular value decomposition of the operator $K_q^A(\rho_1, r)$ which follows from the identity of equation (24) and is of the form $$K_q^A(\rho_1, r) = \int d^2 q' \sigma_{q'}^A g_{q'}(\rho_1) f_{q'}^{A*}(r) \quad (35)$$

where $$g_{q'}(\rho) = \frac{1}{2\pi} e^{iq' \cdot \rho} \quad (36)$$

$$f_{q'}^A(r) = \frac{N_{q'}}{2\pi} e^{i((q'-q)\cdot\rho + \theta_{q'})} \exp\left[-\left((q^2+k^2)^{\frac{1}{2}} + (q'^2+k^2)^{\frac{1}{2}}\right)^* |z|\right] \quad (37)$$

and $$\sigma_{q'}^A = \frac{1}{4 D_0^2 N_{q'}} |q^2 + k^2|^{-\frac{1}{2}} |q'^2 + k^2|^{-\frac{1}{2}} \quad (38)$$

with $$\tan(2\theta_{q'}^A) = \frac{\tan(2\theta_q) + \tan(2\theta_{q'})}{1 - \tan(2\theta_q)\tan(2\theta_{q'})}. \quad (39)$$

$$N_{q'}^2 = \frac{1}{2}\left((q^2+k^2)^{\frac{1}{2}} + (q'^2+k^2)^{\frac{1}{2}}\right) + \text{complex conjugate} \quad (40)$$

This result may be used to obtain the solution to the integral equation (34) in the form $$\delta\alpha(r) = \int d^2 \rho_1 \int d^2 q' \frac{1}{\sigma_{q'}^A} g_{q'}^*(\rho_1) f_{q'}^A(r) \phi_q(\rho_1). \quad (41)$$

We now turn to the problem of reconstructing the diffusion coefficient of a medium with a spatially uniform absorption coefficient. Equation (15) thus becomes $$\phi_q(\rho_1) = \int d^3 r K_q^D(\rho_1, r) \delta D(r). \quad (42)$$

As before, it follows that $K_q^D(\rho_1, r)$ is given by the singular value decomposition $$K_q^D(\rho_1, r) = \int d^2 q' \sigma_{q'}^D g_{q'}(\rho_1) f_{q'}^{D*}(r) \quad (43)$$

with the singular values $$\sigma_{q'}^D = \frac{1}{4 D_0^2 N_{q'}} |q^2+k^2|^{-\frac{1}{2}} |q'^2+k^2|^{-\frac{1}{2}} \left| q \cdot q' + (q^2+k^2)^{\frac{1}{2}} (q'^2+k^2)^{\frac{1}{2}} \right| \quad (44)$$

and $f_q^D(r) = e^{i(\theta_{qD} - \theta_{qA})} f_q^A(r)$. Thus the solution to the integral equation (42) is given by $$\delta D(r) = \int d^2 \rho_1 \int d^2 q' \frac{1}{\sigma_{q'}^D} g_{q'}^*(\rho_1) f_{q'}^D(r) \phi_q(\rho_1). \quad (45)$$

Finally, we consider the general case of reconstructing both the absorption and diffusion coefficients. We require the solution to the integral equation (15) which is given by $$\delta\alpha = K_q^{A*}(K_q^A K_q^{A*} + K_q^D K_q^{D*})^{-1} \phi_q \quad (46)$$

and $$\delta D = K_q^{D*}(K_q^A K_q^{A*} + K_q^D K_q^{D*})^{-1} \phi_q. \quad (47)$$

Since $K_q^A K_q^{A*}$ and $K_q^D K_q^{D*}$ commute, we may now use the singular value decompositions of $K_q^A$ and $K_q^D$ to rewrite equations (46) and (47) as $$\delta\alpha(r) = \int d^2 \rho_1 \int d^2 q' \sigma_{q'}^A (\sigma_{q'}^{A2} + \sigma_{q'}^{D2})^{-1} g_{q'}^*(\rho_1) f_{q'}^A(r) \phi_q(\rho_1) \quad (48)$$

and $$\delta D(r) = \int d^2 \rho_1 \int d^2 q' \sigma_{q'}^D (\sigma_{q'}^{A2} + \sigma_{q'}^{D2})^{-1} g_{q'}^*(\rho_1) f_{q'}^D(r) \phi_q(\rho_1) \quad (49)$$

which is the inversion formula for the inverse problem with scattering data determined by a single wavevector.

B. Multiple Wavevector Solutions

Consider p measurements corresponding to the wavevectors $q_1, \ldots, q_p$. Then the image reconstruction problem consists of solving the system of integral equations $$K_{q_k}^A \delta\alpha + K_{q_k}^D \delta D = \phi_{q_k} \quad (50)$$

with $k=1, \ldots, p$. It is useful to rewrite equation (50) as $$K_{q_k} f = \phi_{q_k} \quad (51)$$

where the vector operator $K_{q_k} = (K_{q_k}^A, K_{q_k}^D)$ and $f = (\delta\alpha, \delta D)^T$. To solve equation (51) we introduce the orthogonal projection operators $P_k$ onto the solution spaces $F_k = \{f : K_{q_k} f = \phi_{q_k}\}$. Then the solution to equation (51) can be obtained by successive projections onto the $F_k$ thereby defining a sequence of functions $f_n$ which converges to the solution to equation (51). Thus, the solution to equation (50) is given by $$f_{n+1} = \prod_k P_k f_n \quad (52)$$

with $n=1,2,\ldots$ and $f_1$ arbitrary. To make further progress we require an explicit form for the projection operator $P_k$. This is given by $$P_k f = f + K_{q_k}^*(K_{q_k} K_{q_k}^*)^{-1}(\phi_{q_k} - K_{q_k} f). \quad (53)$$

Using this result and equation (52) we obtain the recursion relation $$f_n^{k+1} = f_n^k + K_{q_k}^*(K_{q_k} K_{q_k}^*)^{-1}(\phi_{q_k} - K_{q_k} f_n^k) \quad (54)$$

where $f_n^1 \equiv f_n$ and $f_n^{p+1} \equiv f_{n+1}$. We now rewrite equation (54) as $$\delta\alpha_n^{k+1} = \delta\alpha_n^k + K_{q_k}^{A*}(K_{q_k}^A K_{q_k}^{A*} + K_{q_k}^D K_{q_k}^{D*})^{-1}(\phi_{q_k} - K_{q_k}^A \delta\alpha_n^k - K_{q_k}^D \delta D_n^k) \quad (55)$$

and $$\delta D_n^{k+1} = \delta D_n^k + K_{q_k}^{D*}(K_{q_k}^A K_{q_k}^{A*} + K_{q_k}^D K_{q_k}^{D*})^{-1}(\phi_{q_k} - K_{q_k}^A \delta\alpha_n^k - K_{q_k}^D \delta D_n^k) \quad (56)$$

Finally, we use the singular value decompositions of $K_{q_k}^A$ and $K_{q_k}^D$ to obtain our main result $$\delta\alpha_n^{k+1}(r) = \delta\alpha_n^k(r) + \int d^2 \rho_1 \int d^2 q \sigma_{qq_k}^A (\sigma_{qq_k}^{A\ 2} + \sigma_{qq_k}^{D\ 2})^{-1} g_{qq_k}^*(\rho_1) f_{qq_k}^A(r) \times (\phi_{q_k}(\rho_1) - K_{q_k}^A \delta\alpha_n^k(\rho_1) - K_{q_k}^D \delta D_n^k(\rho_1)) \quad (57)$$

and $$\delta D_n^{k+1}(r) = \delta D_n^k(r) + \int d^2 \rho_1 \int d^2 q \sigma_{qq_k}^D (\sigma_{qq_k}^{A\ 2} + \sigma_{qq_k}^{D\ 2})^{-1} g_{qq_k}^*(\rho_1) f_{qq_k}^D(r) \times (\phi_{q_k}(\rho_1) - K_{q_k}^A \delta\alpha_n^k(\rho_1) - K_{q_k}^D \delta D n^k(\rho_1)) \quad (58)$$

which provides an explicit solution to the inverse scattering problem with diffusing waves. Note that we have indicated the dependence of the singular values and singular functions on the wavevectors $q_k$. Observe also that each iterative step of the inversion procedure is similar in form to the single-wavevector case considered previously.

C. Multiple Wavevector Solutions by Singular Value Decomposition

In this section we consider an alternative approach to the multiple wavevector inverse problem. Rather than solving integral equations (50) by an iterative method we obtain the solution by singular value decomposition. To begin we rewrite equation (50) as $$Kf = \phi \tag{59}$$

where $$K = \begin{bmatrix} K_{q^2}^A & K_{q^2}^D \\ \vdots & \vdots \\ K_{q^p}^A & K_{q^p}^D \end{bmatrix} \tag{60}$$

and $\phi = (\phi_{q^1}, \ldots, \phi_{q^p})^T$. The solution to equation (59) follows from the singular value decomposition of the operator $K(\rho_1, r)$ which is given by $$K(\rho_1, r) = \int d^2 q \sum_m \sigma_{qm} \phi_{qm}(\rho_1) \psi_{qm}^*(r) \tag{61}$$

where $m = 1, \ldots, p$. Here the singular functions $\phi_{qm}(\rho_1)$ and $\psi_{qm}(r)$, and singular values $\sigma_{qm}$ are defined by $$KK^* \phi_{qm} = \sigma_{qm}^2 \phi_{qm} \tag{62}$$

and $$K^* \phi_{qm} = \sigma_{qm} \psi_{qm}. \tag{63}$$

To obtain the $\phi_{qm}$ we rewrite equation (62) as $$\sum_{j=1}^{m} (K_{q^k}^A K_{q^j}^{A*} + K_{q^k}^D K_{q^j}^{D*}) \phi_{qmj} = \sigma_{qm}^2 \phi_{qmi} \tag{64}$$

where $\phi_{qmj} = (\phi_{qm})_j$. Then we use singular value decompositions of equations (25) and (42) to obtain the identities $$K_{q^k}^A K_{q^j}^{A*} g_{qqj} = \chi_{kj}^A(q) \sigma_{qq^k}^A \sigma_{qq^j}^A g_{qq^k} \tag{65}$$

and $$K_{q^k}^D K_{q^j}^{D*} g_{qqj} = \chi_{kj}^D(q) \sigma_{qq^k}^D \sigma_{qq^j}^D g_{qq^k}. \tag{66}$$

The overlap functions $\chi_{kj}^A(q)$ and $\chi_{kj}^D(q)$ are defined by $$\langle f_{qq^k}^A, f_{q'q^j}^A \rangle = \chi_{kj}^A(q) \delta(q-q') \tag{67}$$

and $$\langle f_{qq^k}^D, f_{q'q^j}^D \rangle = \chi_{kj}^D(q) \delta(q-q') \tag{68}$$

where we have introduced the notation $f_{qq^k}^{A,D}(r) = f_{q+q^k}^{A,D}(r)$, $g_{qq^k}(\rho) = g_{q+q^k}(\rho)$, and $\sigma_{qq^k}^{A,D} = \sigma_{q+q^k}^{A,D}$. Next, if we put $\phi_{qmj} = c_{mj}(q) g_{qq^j}$, and use equations (64)–(66) we find that the $c_{mj}(q)$ satisfy the equation $$\sum_j M_{kj}(q) c_{mj}(q) = \sigma_{qm}^2 c_{mk}(q) \tag{69}$$

where $$M_{kj}(q) = \chi_{kj}^A(q) \sigma_{qq^k}^A \sigma_{qq^j}^A + \chi_{kj}^D(q) \sigma_{qq^k}^D \sigma_{qq^j}^D. \tag{70}$$

Note that $c_m(q)$ is an eigenvector of $M_{kj}(q)$ with eigenvalue $\sigma_{qm}^2$ and that since $M_{kj}(q)$ is symmetric we can choose the $c_m(q)$ to be orthonormal. Finally, we use equation (63) to obtain the $\psi_{qm}(r)$, whose components we label with an A or D, and which are given by $$\psi_{qm}^A(r) = \frac{1}{\sigma_{qm}} \sum_j \sigma_{qq^j}^A c_{mj}(q) f_{qq^j}^A(r) \tag{71}$$

and $$\psi_{qm}^D(r) = \frac{1}{\sigma_{qm}} \sum_j \sigma_{qq^j}^D c_{mj}(q) f_{qq^j}^D(r). \tag{72}$$

The solution to equation (59) may now be expressed as $$f(r) = \int d^2 \rho_1 K^+(r, \rho_1) \phi(\rho_1) \tag{73}$$

where $$K^+(r, \rho_1) = \int d^2 q \sum_m \frac{1}{\sigma_{qm}} \psi_{qm}(r) \phi_{qm}^*(\rho_1). \tag{74}$$

Using this result we obtain $$\delta\alpha(r) = \int d^2 \rho_1 \int d^2 q \sum_m \frac{1}{\sigma_{qm}} \psi_{qm}^A(r) \phi_{qm}^*(\rho_1) \phi(\rho_1) \tag{75}$$

and $$\delta D(r) = \int d^2 \rho_1 \int d^2 q \sum_m \frac{1}{\sigma_{qm}} \psi_{qm}^D(r) \phi_{qm}^*(\rho_1) \phi(\rho_1) \tag{76}$$

which are the inversion formulas for the inverse scattering problem with diffusing waves.

D. Discussion

Several comments on our results are necessary.

First, the solution we have constructed to the inverse problem is the unique solution of minimum norm given the scattering data. This statement follows from the result that the singular value decomposition provides the solution to equation (15) that belongs to the orthogonal complement of the nullspace of the integral equation. It is important to note that the size of the nullspace is expected to decrease as the number of wavevectors increases, and thus the inversion procedure is systematically improvable.

Second, as previously discussed, the inverse problem is expected to be ill-posed. However, by introducing an appropriate regularization procedure we find that the solution we have obtained to the inverse problem is well behaved. The necessity of a regularization procedure may be understood by observing for large $|q|$ that the singular values of $K_q^A$ and $K_q^D$ are asymptotically given by $\sigma_q^A \sim |q|^{-3/2}$ and $\sigma_q^D \sim |q|^{-1/2}$. Thus the inverse problem is mildly ill-posed. This is of no concern since cutting off the wavevector integration at large $|q|$ effects a regularization of the inverse problem. Note that regularization here has a natural physical interpretation. The cutoff $|q| > 2\pi/l^*$ (with $l^*$ the maximum transport mean free path) simply sets the spatial resolution of the reconstruction to be $l^*$—the length scale on which the diffusion approximation is valid.

Third, the diffusion imaging experiment is carried out in the near field of the diffusing wave even though it is the far field of the electromagnetic wave which is measured at the detector. Thus the expectation from geometrical optics that the spatial resolution of the reconstructed image should be controlled by the wavelength of the diffusing wave is seen to be incorrect in the near field.

Fourth, it is important to appreciate that an algorithm based on equations (57) and (58) has computational complexity $O(N^2)$ where N is the number of pixels in the image. This should be compared with the $O(N^3)$ complexity of a direct numerical inversion of the integral equation by singular value decomposition.

Finally, the proposed inversion method should also be compared with previous approaches to the problem of imaging with multiply-scattered light which effect an indirect inversion of the forward scattering problem by an iterative technique. Such indirect methods have computing times that grow exponentially with the number of volume elements in the reconstructed image.

B. SYSTEM

Figure 6:
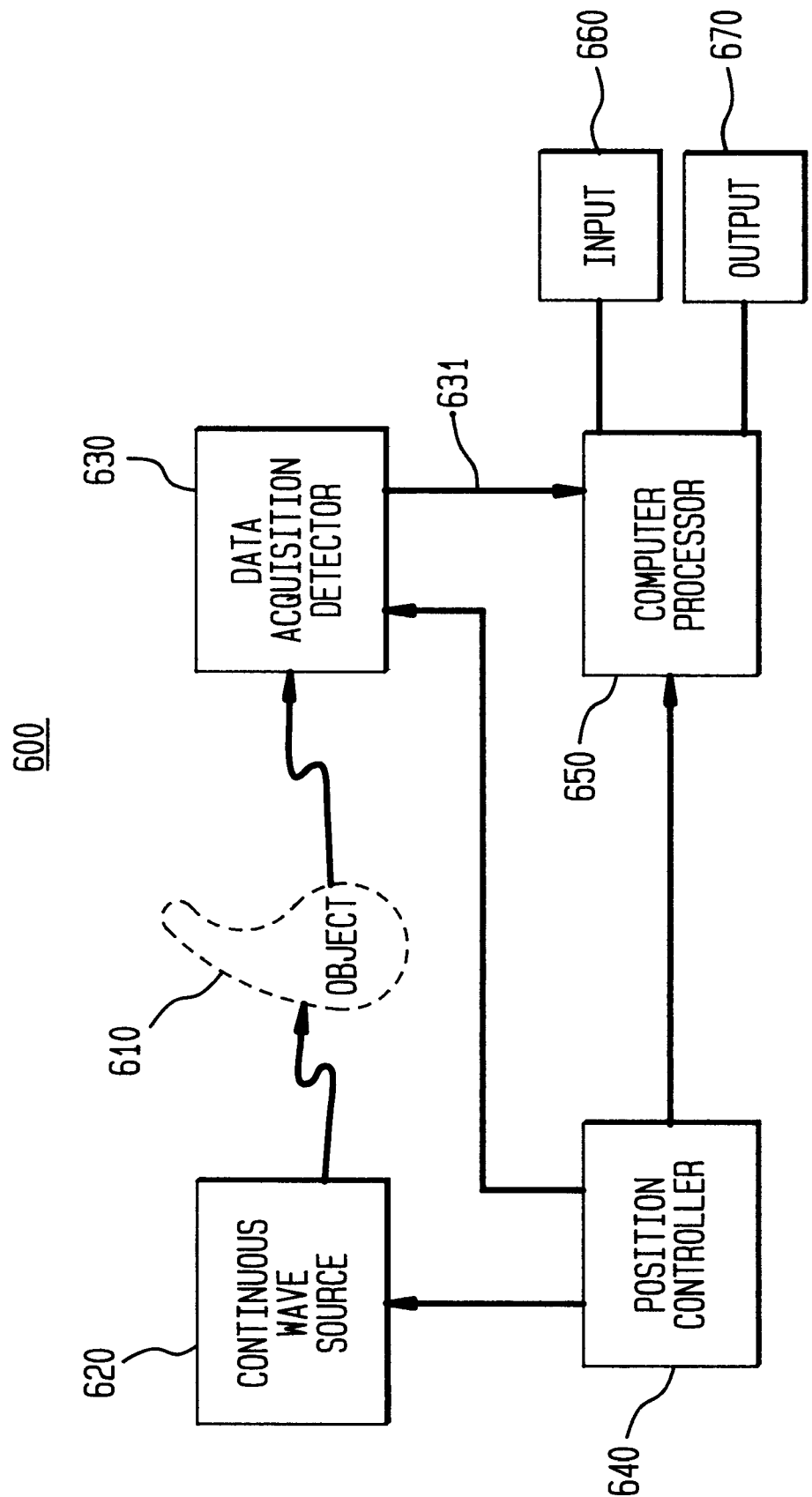
FIG. 6 illustrates a high-level block diagram of one embodiment of the photon imaging system in accordance with the present invention for a frequency-domain implementation.

As depicted in high-level block diagram form in FIG. 6, system 600 is a direct reconstruction imaging system for generating an image of an object using measurements of transmitted radiation (e.g., photons) emanating from an object in response to photons impinging on the object. In particular, object 610 is shown as being under investigation. System 600 is composed of: CW source 620 for irradiating object 610; data acquisition detector 620 for generating the transmitted intensity of radiation emanating from object 610 at one or more strategic locations proximate to object 610, such transmitted intensity being determined from measurements of both the modulus and phase (to obtain $u_{107}(r)$) via a phase-sensitive detector; position controller 640 for controlling the location of detector 630 relative to source 620; and computer processor 650, having associated input device 660 (e.g. a keyboard) and output device 670 (e.g., a graphical display terminal). Computer processor 650 has as its inputs positional information from controller 640 and the measured transmitted intensity from detector 630.

Source 620 and data acquisition detector 630 of system 600 are realized with conventional components; illustratively, Gratton discloses such source and detector arrangements, and the teachings of Gratton with respect to the measurement procedure are hereby incorporated with reference. Thus, for example, CW source 620 is composed of a conventional near infrared laser operating in the 600 to 1200 nm region and at a power level of approximately 10 watts such as provided by a mode-locked Neodymium YAG laser (Antares, model 76S-ML-SHG). Detector 630 is, for instance, composed of a image intensifier (such as provided by Princeton Instruments, Inc., OMA detector model IRY512 G/RB) which feeds a CCD-type television camera (such as provided by ITT, Fort Wayne, Ind., model CCD F144). With the arrangements disclosed by Gratton, both the phase and modulus of the diffusively scattered radiation may be generated.

Position controller 640 is utilized whenever CW source 620 and/or data acquisition detector 630 may be composed of a plurality of radiation sources and detectors, respectively, in order to control which of the plurality of sources may be energized for a given time period and which of the plurality of detectors may be activated during a prescribed time interval. As will be discussed in more detail below, in a practical implementation of the direct reconstruction imaging technique, it is oftentimes necessary to measure the transmitted intensity effected by a number of source-detector positions surrounding object 610. For the sake of expediency, generation of the required transmitted intensity data is expeditiously accomplished by having arrays of P laser sources and Q photon detectors. Accordingly, source 620 may be composed, in its most general implementation, of P CW sources or the like arranged strategically around the periphery of object 610. Similarly, data acquisition detector may be composed, in its most general realization, of Q radiation detectors or the like also arranged strategically around the periphery of object 610 and in a cooperative relation with the P sources.

The point of departure between the inventive subject matter herein and the prior art resides in the processing of the measured data. Computer 650 stores a computer program which implements the direct reconstruction algorithm; in particular, the stored program processes the measured transmitted intensity data to produce the image of the object under study using a prescribed mathematical algorithm; the algorithm is determined with reference to the integral operator relating the transmitted intensity to both the absorption and the diffusion coefficients. The algorithm further relates the absorption and diffusion coefficients to the transmission coefficient by a different integral operator.

C. FLOW DIAGRAMS

Absorption and Diffusion

The methodology of the present invention is set forth in high-level flow diagram 700 in FIG. 7 in terms of the illustrative embodiment of the system shown in FIG. 6. With reference to FIG. 7, the processing effected by control block 710 enables energy source 620 and data acquisition system 630 so as to measure the transmission coefficient emanating from object 610 due to photon source 620. These measurements are passed to computer processor 650 from acquisition system 630 via bus 631. Next, processing block 720 is invoked to compute the scattering data. In turn, processing block 730 computes the Fourier transform of the scattering data. Next, as depicted by processing block 740, the singular value decomposition (SVD) of $K_q^A(\rho_1,r)$ is effected in conformance to the given source-detector geometry. Block 750 is invoked to effect the singular value decomposition of $K_q^D(\rho_1,r)$ in conformance to the given source-detector geometry. Processing block 760 directly computes the absorption image from the reduced scattering data and the SVD of $K_q^A(\rho_1,r)$. Then, processing block 770 directly computes the diffusion image from the reduced scattering data and the SVD of $K_q^D(\rho_1,r)$. As shown by block 780, in the most general case of multiple wavevectors, successive projections are computed which converge to the absorption and diffusion images. The images are presented on output device 670 in a form determined by the user.

The flow diagram of FIG. 7 is shown as being illustrative of the direct reconstruction technique using iteration, that is, flow diagram 700 is illustrative of the multiple wavevector solution. One skilled in the art, using the teachings of flow diagram 700, may readily devise the corresponding flow for the single wavevector solution and, commensurately, for the multiple wavevector solution using singular value decomposition.

The system and methodology described utilizes the free-space model or infinite-medium model. This is appropriate when object 610 is surrounded by an arrangement, such as a thin, rubber-like container filled with a substance (e.g., the commercially available medical product called Intralipid), so that the arrangement provides a spatial extent external to the object that effectively gives rise to a free-space condition surrounding the object. The object's actual boundary (e.g., a human skull during imaging of brain) becomes merely another shape that is determined by the direct reconstruction procedure. Intralipid is useful because it is a colloidal substance wherein particles in the range of 0.5 microns to 2 microns are suspended, and the substance, as packaged, does not rapidly deteriorate; moreover, the l* of such a substance is readily measurable.

Given the teachings of the detailed description, one of ordinary skill in the art may readily apply the direct, mathematical reconstruction technique for other cases, such as a spherical or bi-planar geometry instead of a planar geometry.

D. TIME DOMAIN

The theory developed in the foregoing sections can also be used to treat the case of a pulsed source, that is, source 620 is now a pulsed source. In this case, $S(r,t)=\delta(t)S(r)$, where $\delta(t)$ is an impulse function. If we introduce the Fourier Transform of $U(r,t)$ by $$\hat{U}(r,\omega) = \int_{-\infty}^{\infty} dt e^{i\omega t} U(r,t),$$

we find that $\hat{U}(r,\omega)$ satisfies equation (4); hence, the theoretical basis developed in the foregoing sections may be used directly.

In FIG. 6, a frequency domain version of the system for directly reconstructing the images of interest was depicted. To achieve time domain reconstruction, the block diagram of FIG. 6 may be used as a point of reference to implement a time domain version of the reconstruction system. Essentially, the source 620 and detector 630 have substituted their respective time domain equivalents.

In accordance with such an illustrative embodiment for the time domain, photon source 620 utilizes a tunable laser, Model MIRA-900P available from Coherent Corp. (This laser actually has two other auxiliary devices associated with it: (1) a acoustic-optic pulse picker to slow down the 78 MHz pulse rate to 5 Mhz—an exemplary device is Model 900 available from Coherent Corp.; and (2) another laser to pump the MIRA-900P—an exemplary pump laser is Model INNOVA-45 available from Coherent.)

Also, data acquisition detector 630 utilizes a photon detector exemplified by a streak-scope Model 64-334-02 available from Hamamatsu Corp.

Although the various embodiments which incorporate the teachings of the present invention have been shown and described in detail herein, those skilled in the art can readily devise many other varied embodiments that still incorporate these teachings.

What is claimed is:

1. A method for generating an absorption image of an object comprising the steps of
   - irradiating the object with a source of radiation,
   - measuring a transmission coefficient due predominantly to diffusively scattered radiation wherein said transmission coefficient is related to the absorption coefficient by an integral operator, and
   - directly reconstructing the image by executing a prescribed mathematical algorithm, determined with reference to said integral operator, on said transmission coefficient, said algorithm further relating the absorption coefficient to said transmission coefficient by another integral operator.

2. The method as recited in claim 1 wherein the step of directly reconstructing includes the step of iteratively reconstructing the image.

3. Circuitry for generating an absorption image of an object comprising
   - irradiation means for irradiating the object with a source of radiation,
   - measurement means, responsive to the means for irradiating, for measuring a transmission coefficient due predominantly to diffusively scattered radiation wherein said transmission coefficient is related to the absorption coefficient by an integral operator, and
   - reconstruction means, responsive to the means for measuring, for directly reconstructing the image by executing a prescribed mathematical algorithm, determined with reference to said integral operator, on said transmission coefficient, said algorithm further relating the absorption coefficient to said transmission coefficient by another integral operator.

4. The circuitry as recited in claim 3 wherein the reconstruction means includes means for iteratively reconstructing the image.

5. A method for generating an diffusion image of an object comprising the steps of
   - irradiating the object with a source of radiation,
   - measuring a transmission coefficient due predominantly to diffusively scattered radiation wherein said transmission coefficient is related to the diffusion coefficient by an integral operator, and
   - directly reconstructing the image by executing a prescribed mathematical algorithm, determined with reference to said integral operator, on said transmission coefficient, said algorithm further relating the diffusion coefficient to said transmission coefficient by another integral operator.

6. The method as recited in claim 5 wherein the step of directly reconstructing includes the step of iteratively reconstructing the image.

7. Circuitry for generating an diffusion image of an object comprising
   - irradiation means for irradiating the object with a source of radiation,
   - measurement means, responsive to the means for irradiating, for measuring a transmission coefficient due predominantly to diffusively scattered radiation wherein said transmission coefficient is related to the diffusion coefficient by an integral operator, and
   - reconstruction means, responsive to the means for measuring, for directly reconstructing the image by executing a prescribed mathematical algorithm, determined with reference to said integral operator, on said transmission coefficient, said algorithm further relating the diffusion coefficient to said transmission coefficient by another integral operator.

8. The circuitry as recited in claim 7 wherein the reconstruction means includes means for iteratively reconstructing the image.

9. A method for generating absorption and diffusion images of an object comprising the steps of
   - irradiating the object with a source of radiation,
   - measuring a transmission coefficient due predominantly to diffusively scattered radiation wherein said transmission coefficient is related to the absorption coefficient and diffusion coefficient by an integral operator, and
   - directly reconstructing the images by executing a prescribed mathematical algorithm, determined with reference to said integral operator, on said transmission coefficient, said algorithm further relating the absorption coefficient and the diffusion coefficient to said transmission coefficient by another integral operator.

10. The method as recited in claim 9 wherein the step of directly reconstructing includes the step of iteratively reconstructing the image.

11. Circuitry for generating absorption and diffusion images comprising
   - irradiation means for irradiating the object with a source of radiation,
   - measurement means, responsive to the means for irradiating, for measuring a transmission coefficient due predominantly to diffusively scattered radiation wherein said transmission coefficient is related to the absorption coefficient and the diffusion coefficient by an integral operator, and reconstruction means, responsive to the means for measuring, for directly reconstructing the images by executing a prescribed mathematical algorithm, determined with reference to said integral operator, on said transmission coefficient, said algorithm further relating the absorption coefficient and the diffusion coefficients to said transmission coefficient by another integral operator.

12. The circuitry as recited in claim 11 wherein the reconstruction means includes means for iteratively reconstructing the image.

* * * * *